(12) United States Patent
Lipowicz (10) Patent No.: US 11,357,936 B2
(45) Date of Patent: Jun. 14, 2022

(54) METHOD AND DEVICES FOR CONTROLLING ELECTRONIC VAPING DEVICES

(71) Applicant: Altria Client Services LLC, Richmond, VA (US)

(72) Inventor: Peter J. Lipowicz, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 924 days.

(21) Appl. No.: 15/053,181

(22) Filed: Feb. 25, 2016

(65) Prior Publication Data
US 2017/0245547 A1  Aug. 31, 2017

(51) Int. Cl.
| | |
|---|---|
| *A24F 40/53* | (2020.01) |
| *A24F 40/51* | (2020.01) |
| *A24F 40/50* | (2020.01) |
| *A24F 40/60* | (2020.01) |
| *H05B 1/02* | (2006.01) |
| *A61M 15/06* | (2006.01) |
| *A61M 15/00* | (2006.01) |

(Continued)

(52) U.S. Cl.
CPC .............. *A61M 15/06* (2013.01); *A24F 40/50* (2020.01); *A24F 40/51* (2020.01); *A24F 40/53* (2020.01); *A24F 40/60* (2020.01); *A61M 11/042* (2014.02); *A61M 15/008* (2014.02); *A61M 15/0081* (2014.02); *H05B 1/0222* (2013.01); *H05B 1/0244* (2013.01); *H05B 3/0014* (2013.01); *A61M 2016/0024* (2013.01); *A61M 2016/0027* (2013.01); *A61M 2205/332* (2013.01); *A61M 2205/3584* (2013.01); *A61M 2205/52* (2013.01); *A61M 2205/587* (2013.01); *A61M 2205/8206* (2013.01); *A61M 2205/8237* (2013.01)

(58) Field of Classification Search
None
See application file for complete search history.

(56) References Cited

U.S. PATENT DOCUMENTS

| | | |
|---|---|---|
| 8,156,944 B2 | 4/2012 | Han |
| 8,757,147 B2 | 6/2014 | Terry et al. |

(Continued)

FOREIGN PATENT DOCUMENTS

| | | |
|---|---|---|
| CN | 203841114 U | 9/2014 |
| CN | 104432537 A | 3/2015 |

(Continued)

OTHER PUBLICATIONS

ECig One Staff. "How to Use an E-Cigarette". eCig One: E-Cigarette Reviews and News You Can Trust. 2015. http://ecigone.com/e-cigarette-basics/how-to-use-e-cigarette/.

(Continued)

*Primary Examiner* — Michael J Felton
(74) *Attorney, Agent, or Firm* — Harness, Dickey & Pierce, P.L.C.

(57) ABSTRACT

According to at least one example embodiment, a controller for an e-vaping device includes a movement sensor configured to detect movement of the e-vaping device and output an output signal based on the movement. The controller includes control circuitry configured to control power supplied to power consuming elements of the e-vaping device based on the output signal.

17 Claims, 8 Drawing Sheets

(51) Int. Cl.
　　　*A61M 11/04*　　　(2006.01)
　　　*H05B 3/00*　　　(2006.01)
　　　*A61M 16/00*　　　(2006.01)

(56) References Cited

U.S. PATENT DOCUMENTS

| | | |
|---|---|---|
| 2006/0196518 A1 | 9/2006 | Hon |
| 2008/0257367 A1 | 10/2008 | Paterno et al. |
| 2011/0036346 A1 | 2/2011 | Cohen et al. |
| 2013/0081642 A1 | 4/2013 | Safari |
| 2013/0284192 A1 | 10/2013 | Peleg et al. |
| 2013/0340775 A1 | 12/2013 | Juster et al. |
| 2014/0096781 A1 | 4/2014 | Sears et al. |
| 2014/0107815 A1 | 4/2014 | LaMothe |
| 2014/0366898 A1 | 12/2014 | Monsees et al. |
| 2015/0257445 A1 | 9/2015 | Henry, Jr. et al. |
| 2016/0259459 A1* | 9/2016 | Yang .......................... G06F 3/16 |

FOREIGN PATENT DOCUMENTS

| | | |
|---|---|---|
| CN | 104582774 A | 4/2015 |
| CN | 104621716 A | 5/2015 |
| RU | 103062 U1 | 3/2011 |
| WO | WO-2014/066730 A1 | 5/2014 |
| WO | WO-2015/138560 A1 | 9/2015 |
| WO | WO-2016/009202 A1 | 1/2016 |
| WO | WO-2016/094225 A1 | 6/2016 |
| WO | WO-2017/001817 A1 | 1/2017 |

OTHER PUBLICATIONS

International Search Report and Written Opinion for International Application No. PCT/EP/2017/054410 dated May 15, 2017.
CA First Office Action dated Sep. 2, 2020 in Chinese Application No. 201780009196.2.
Decision to Grant dated May 14, 2020 in Russian Application No. 2018133600/12(055192).
Search Report dated May 14, 2020 in Russian Application No. 2018133600(055192).
Decision to Grant a Patent dated Mar. 1, 2021 in Japanese Application No. 2018-543219.

* cited by examiner

METHOD AND DEVICES FOR CONTROLLING ELECTRONIC VAPING DEVICES

BACKGROUND

Field

At least some example embodiments relate generally to an electronic vaping (e-vaping) device.

Related Art

Electronic vaping devices are used to vaporize a pre-vapor formulation into a vapor. These electronic vaping devices may be referred to as e-vaping devices. E-vaping devices include a heater, which vaporizes the pre-vapor formulation to produce the vapor. The e-vaping device may include several e-vaping elements including a power source, a cartridge or e-vaping tank including the heater and a reservoir capable of holding the pre-vapor formulation.

SUMMARY

At least one example embodiment relates to methods and devices for controlling e-vaping devices.

According to at least one example embodiment, a controller for an e-vaping device includes a movement sensor configured to detect movement of the e-vaping device and output an output signal based on the movement. The controller includes control circuitry configured to control power supplied to power consuming elements of the e-vaping device based on the output signal.

According to at least one example embodiment, the movement sensor is an accelerometer.

According to at least one example embodiment, the control circuitry is configured to detect, from the movement, movement events based on a magnitude of the output signal.

According to at least one example embodiment, the control circuitry is configured to count a number of the detected movement events based on a number of times that the magnitude of the output signal exceeds at least one threshold value within an expiration time associated with the at least one threshold value.

According to at least one example embodiment, the control circuitry is configured to identify an operating event based on the counted number of detected movement events.

According to at least one example embodiment, the control circuitry is configured to identify the operating event based on the counted number of detected movement events and at least one of the expiration time, the at least one threshold value, the magnitude of the output signal, a direction of the movement, and time stamps associated with the counted number of detected movement events.

According to at least one example embodiment, the control circuitry is configured to consult a table stored in a storage medium to identify the operating event.

According to at least one example embodiment, the control circuitry is configured to supply power to desired ones of the power consuming elements based on the identified operating event.

According to at least one example embodiment, the power consuming elements include at least one of a battery level indicator for indicating a level of the battery, a lock-out circuit for locking and unlocking the e-vapor device, and an indicator for indicating an amount of the pre-vapor formulation.

According to at least one example embodiment, an e-vaping device includes a reservoir configured to store a pre-vapor formulation. The e-vaping device includes a vaporizer configured to generate a vapor from the pre-vapor formulation and a pow supply configured to supply power to poi consuming elements of the e-vapor device. The power consuming elements may include the vaporizer. The e-vaping device may include a movement sensor configured to detect movement of the e-vaping device and output an output signal based on the movement. The e-vaping device may include control circuitry configured to control the power supplied to the power consuming elements based on the output signal.

According to at least one example embodiment, the movement sensor is an accelerometer.

According to at least one example embodiment, the vaporizer includes a porous element in fluid communication with the reservoir, and a heater configured to vaporize pre-vapor formulation in the porous element.

According to at least one example embodiment, the control circuitry is configured to detect, from the movement, movement events based on a magnitude of the output signal.

According to at least one example embodiment, the control circuitry is configured to count a number of the detected movement events based on a number of times that the magnitude of the output signal exceeds at least one threshold value within an expiration time associated with the at least one threshold value.

According to at least one example embodiment, the control circuitry is configured to identify an operating event based on the counted number of detected movement events.

According to at least one example embodiment, the control circuitry is configured to identify the operating event based on the counted number of detected movement events and at least one of the expiration time, the at least one threshold value, the magnitude of the output signal, a direction of the movement, and time stamps associated with the counted number of detected movement events.

According to at least one example embodiment, the control circuitry is configured to consult a table stored in a storage medium to identify the operating event.

According to at least one example embodiment, the control circuitry is configured to supply power to desired ones of the power consuming elements based on the identified operating event.

According to at least one example embodiment, the power consuming elements include at least one of a battery level indicator for indicating a level of the battery, a lock-out circuit for locking and unlocking the e-vapor device, and an indicator for indicating an amount of the pre-vapor formulation.

BRIEF DESCRIPTION OF THE DRAWINGS

The above and other features and advantages of example embodiments will become more apparent by describing, example embodiments in detail with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Some detailed example embodiments are disclosed herein. However, specific structural and functional details disclosed herein are merely representative for purposes of describing ex pie embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Figure 1:
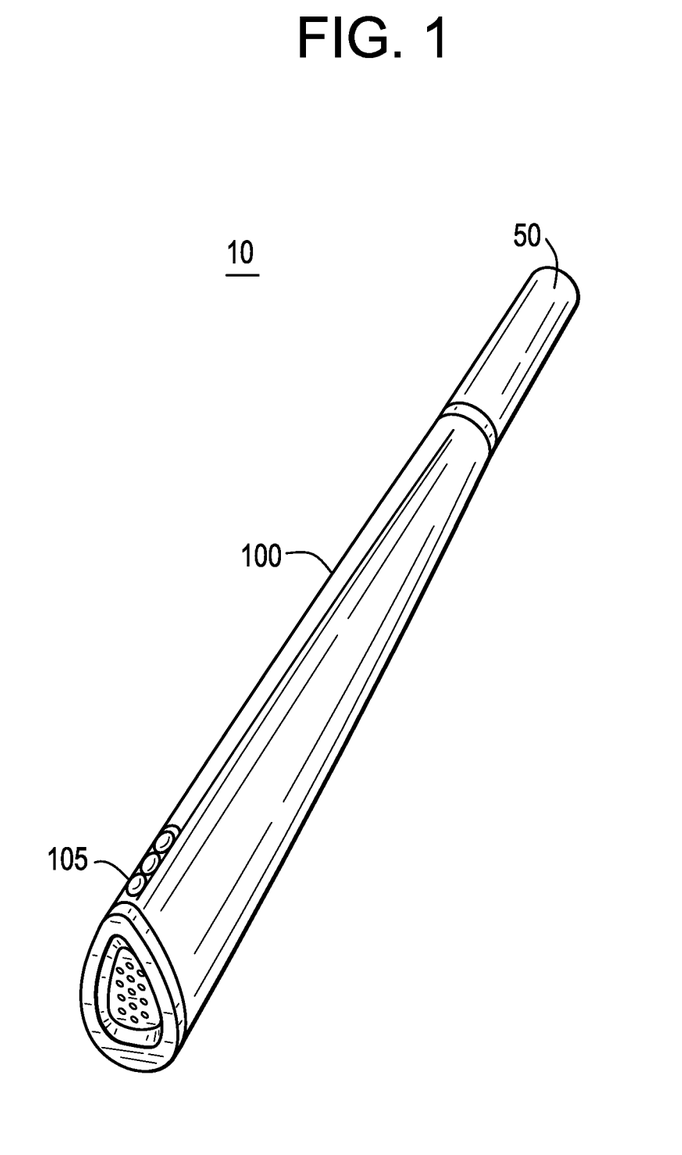
FIG. 1 illustrates an electronic vaping device including a reusable section and a cartridge section according to an example embodiment.

Referring to FIG. 1, an electronic vaping (e-vaping) device 10 includes a cartridge (or first section, or cartridge section) 50, a power section (or second section, or power supply section) 100 and lighting indicators 105.

The lighting indicators 105 may be controlled by a controller and indicate a status of the e-vaping device 10. The lighting indicators 105 may be three light-emitting diodes (LEDs) that are used in various sequences to illustrate at least the following states of the e-vaping device 10: Cartridge Detected, Cartridge Detected, Puff, Battery Level, Disabled Mode, Enables Mode, Cartridge Error and Battery Error.

The first section 50 and the second section 100 may be coupled together at a connection using a connector. The connector may include a male connecting portion and a female connecting portion. The male connecting portion may be secured to one of the first section 50 and the second section 100. The male connecting portion may include a pair of mating arms extending from a rim of the male connecting portion. The pair of mating arms and the rim may define a pair of angled slots there between. A terminus of each of the pair of angled slots includes an enlarged socket end. The female connecting portion is secured to the other of the first section 50 and the second section 100. For example, when the male connecting portion is secured to the first section 50, the female connecting portion is secured to the second section 100 (and vice versa). The female connecting portion may include an inner surface and a pair of lugs on the inner surface. The female connecting portion is configured to longitudinally and rotationally receive the pair of mating arms of the male connecting portion so as to engage each of the pair of lugs of the female connecting portion within the enlarged socket end of each of the pair of angled slots of the male connecting portion to electrically couple the first section 50 and the second section 100 (see the discussion of FIGS. 3A-3B for further detail regarding the connection of the first section 50 and the second section 100).

The second section 100 may also include a pressure sensor to monitor a pressure within the second section 100, a power supply and a controller configured to control and interpret data from the pressure sensor.

Figure 3A:
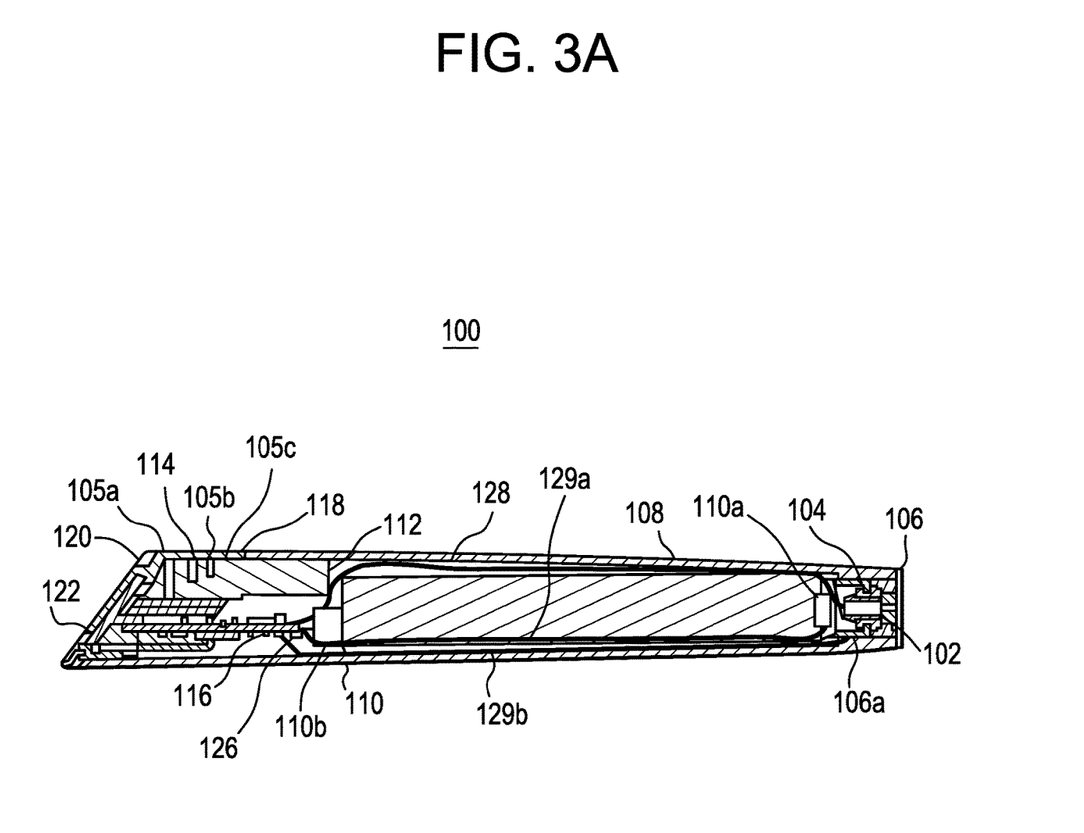
FIG. 3A illustrates a cross-sectional view of an example embodiment of the reusable section shown in FIG. 1.
Figure 3B:
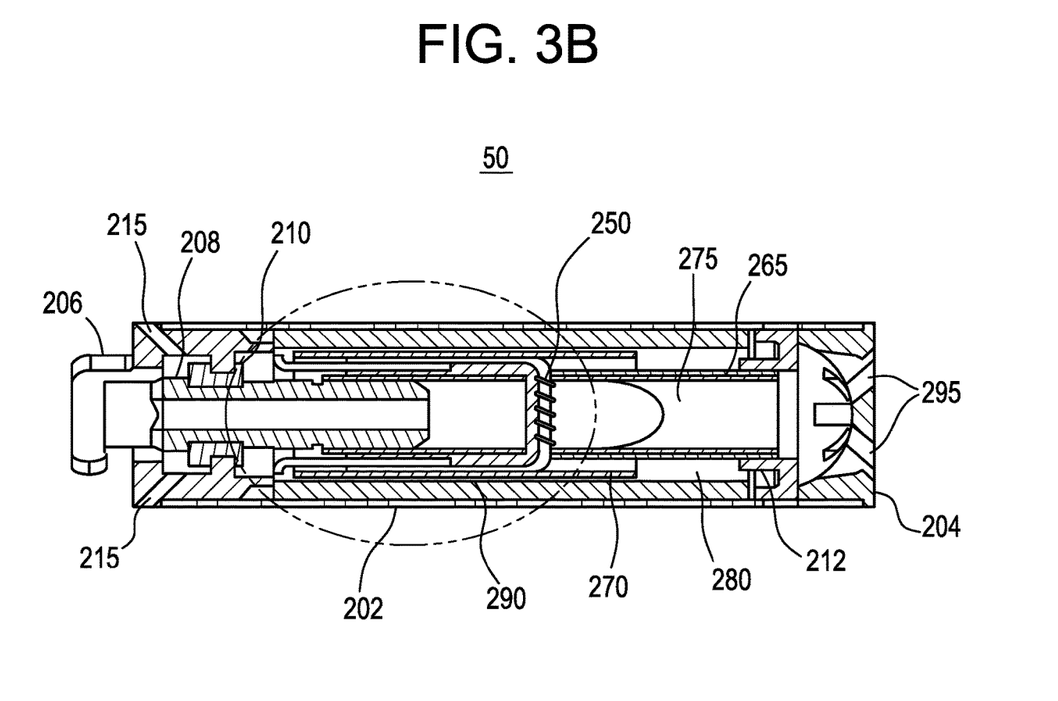
FIG. 3B illustrates a cross-sectional view of an example embodiment of the cartridge section shown in FIG. 1.
Figure 3C:
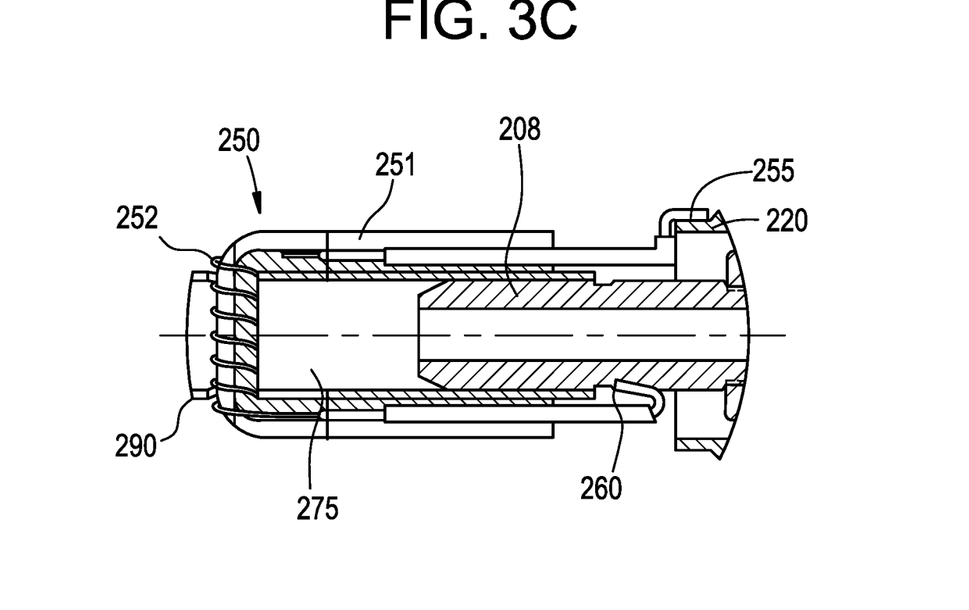
FIG. 3C illustrates a close-up cross-sectional view of an example embodiment of the cartridge section within the dashed lines of FIG. 3B.

The first section 50 may include a vaporizer configured to heat a pre-vapor formulation to generate a vapor (see discussion of FIG. 3C). A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol. The battery assembly is configured to power the vaporizer assembly.

Figure 2:
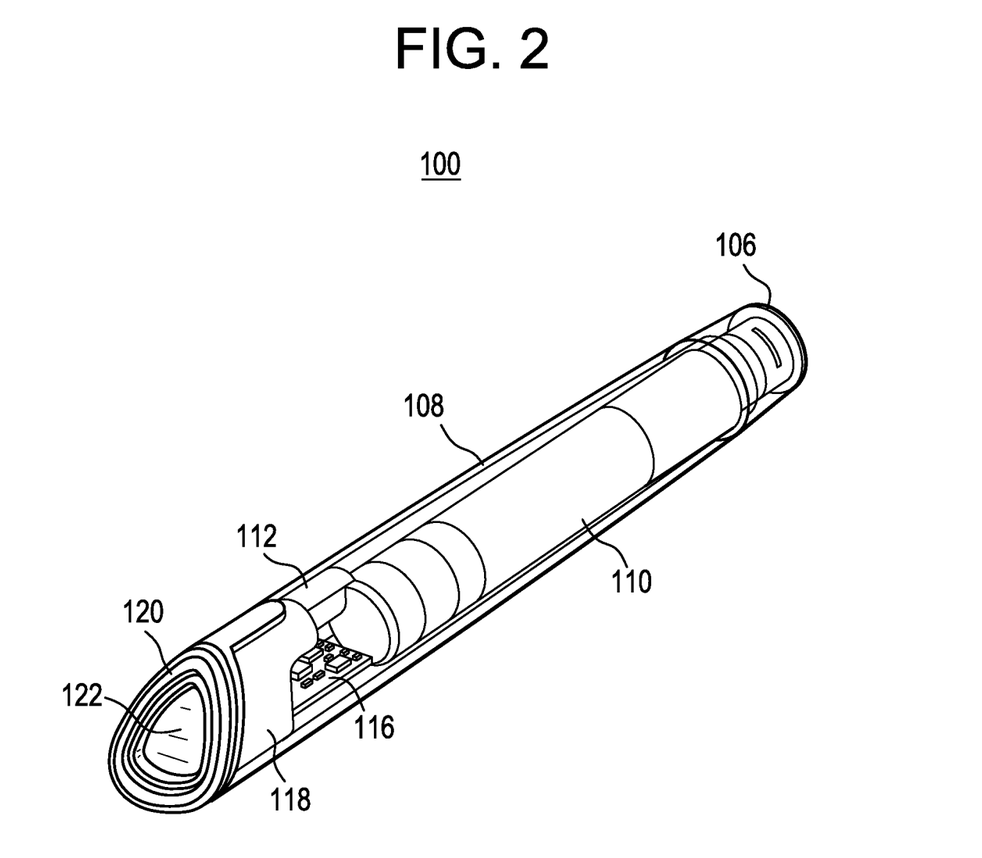
FIG. 2 illustrates a semi-transparent view of an example embodiment of the reusable section shown in FIG. 1.

FIG. 2 illustrates a semi-transparent view of the second section 100. As shown in FIG. 2, the second section 100 includes a female connecting portion 106, a housing 108, a power supply (or battery) 110, a light pipe assembly 112, a printed circuit board (PCB) 116, an end cap 118, a positive contact 120 and a common contact 122. The light pipe assembly 112 includes a light article (e.g., a light pipe) 114 which holds lighting indicators.

A female connecting portion 106 is disposed at a proximal end of the housing shell 108, while the end cap 118, the first contact 120 (e.g., positive contact), and the second contact 122 (e.g., common contact) are disposed at an opposing, distal end of the housing shell 108. The second section 100 has a proximal end (adjacent to the female connecting portion 106) with a cylindrical shape that transitions into a triangular form at the opposing, distal end (adjacent to the second contact 122). For instance, the opposing, distal end may have a cross-sectional shape that resembles a Reuleaux triangle. A Reuleaux triangle is a shape formed from the intersection of three circles, each having its center on the boundary of the other two. The battery assembly 100 may also have a slanted end face (relative to the longitudinal axis of the battery assembly 100). However, it should be understood that example embodiments may have other configurations and are not limited to the above forms.

The female connecting portion 106 provides a connection to the first section 50. The female connecting portion 106 is made of a conductive material to provide an electrical connection between the second section 100 and the first section 50. For example, the female connecting portion 106 may have a base made of brass that is plated with nickel and then top plated with silver.

More specifically, upon completing the connection to the first section 50, the power supply 110 is electrically connected with a heater element of the first section 50 upon sensing negative pressure applied by an adult viper by a pressure sensor (see discussion of FIGS. 3A-3C for further detail regarding the electrical connection of the first section 50 to the second section 100). Air is drawn primarily into a central air passage of the first section 50 through one or more air inlets of the e-vaping device 10 (see FIG. 3B). Example embodiments are not limited to e-vaping devices using a pressure sensor to activate the vaping. Rather, example embodiments are also applicable to e-vaping devices that utilize another means for activation, such as a push button or a capacitive button.

The power supply 110 may be operably connected to the heater (as described below with reference to FIGS. 3A-3D) to apply a voltage across the heater. Furthermore, the power supply 110 supplies power to a controller on the circuit board 116, as will be described in greater detail below (see discussion of FIG. 5 for further detail about the circuit board 116).

The power supply 110 may be a Lithium-ion battery or one of its variants, for example a Lithium-ion polymer battery. Alternatively, the power supply 110 may be a Nickel-metal hydride battery, a Nickel cadmium battery, a Lithium-manganese battery, a Lithium-cobalt battery or a fuel cell. In that case, the e-vaping device 10 is usable until the energy in the power supply 110 is depleted or below a set threshold. The power supply 110 may be rechargeable and the circuit board 116 includes circuitry allowing the battery to be chargeable by an external charging device.

FIG. 3A illustrates a cross-sectional view of the second section 100. Referring to FIG. 3A, the second section 100 may increase in size from the proximal end (adjacent to the female connecting portion 106) to the opposing, distal end (adjacent to the second contact 122). The female anode 102 and a female insulating member 104 may be disposed within the female connecting portion 106. The female insulating member 104 may be an annular structure, with the female anode 102 extending there through. For instance, the female anode 102 may be arranged concentrically within the female connecting portion 106 while being electrically isolated therefrom via the female insulating member 104.

As shown in FIG. 3, the power supply 110 may include a battery arranged in the e-vaping device 10 such that a cathode 110a of the power supply 110 may be downstream of an anode 110b of the power supply 110. The cathode 110a is connected to the PCB 116 by a wire 129a. The PCB 116 is then connected to the cathode portion 106a by a wire 129b. More specifically, the anode 110b is connected to the circuitry of the PCB 116 by a wire 126. The circuitry on the PCB 116 acts as a switch to connect the anode 110b of the power supply 110 to the anode portion 102 of the female connecting portion 106, and the cathode 110a of the power supply 110 to the cathode portion 106a. When the PCB circuitry enables the switch, current is allowed to flow though this circuitry if the anode portion 102 is connected to an acceptable circuit (e.g., the circuit of the first section 50).

It should be understood that the locations of the cathode portion 106a and the anode portion 102 may be switched within the female connecting portion 106.

The housing 108 may be made of a plastic and plated with aluminum and coated with gunmetal pigment. The housing 108 extends in a longitudinal direction and houses the power supply 110, the light pipe assembly 112 and the circuit board 116. The female connecting portion 106 and the end cap 118 are provided at opposing ends of the housing 108. The positive contact 120 and common contact 122 are formed on an exposed face of the end cap 118. Both the positive contact 120 and the common contact 122 may be coated with stainless nickel silver.

A light article 114 (e.g., light pipe) may be disposed in the distal end of the second section 100. The light article 114 contains light indicators 105a-105c that are configured to emit a light that is visible to an adult viper based on the state of the e-vapor device. In an example embodiment, the light indicators 105a-105c may emit a light of a first color during vaping, a light of a second color when the power supply 110 is running low, and/or a light of a third color when the power supply 110 is being charged. In lieu of (or in addition to) colored lights, the light indicators 105a-105c may emit a flashing light and a pattern of lights as a status indicator.

For example, the light indicators 105a-105c may be light-emitting diodes (LEDs) that are used in various sequences to illustrate at least the following states: Cartridge Detected, Cartridge Detected, Puff, Battery Level, Disabled Mode, Enabled Mode, Cartridge Error and Battery Error.

The positive contact 120 and the common contact 122 may be connected to the circuit board 116 by wires. The positive contact 120 and the common contact 122 are connected to the circuit board 116 in such a fashion as to permit a charger to communicate with the controller on the circuit board 116 and supply power to the power supply 110. More specifically, when the second section 100 is inserted into a charger, two prongs of the charger, the common contact and the positive contact form a closed circuit.

FIG. 3B illustrates a cross-sectional view of an example embodiment of the first section shown in FIG. 1. Referring to FIG. 3B, the first section (or cartridge section, or cartridge) 50 includes a housing barrel 202 with a proximal end and an opposing, distal end. The housing barrel 202 may be formed of metal (e.g., stainless steel), although other suitable materials may be used. A mouthpiece 204 and a sealing ring 212 are disposed at the proximal end of the housing barrel 202, while a male connecting portion 206 (e.g., vaporizer connector) is disposed at the opposing, distal end of the housing barrel 202. A male anode 208 (e.g., post) and a male insulating member 210 (e.g., gasket ring) may be disposed within the male connecting portion 206. The male insulating member 210 may be an annular structure, with the male anode 208 extending therethrough. For instance, the male anode 208 may be arranged concentrically within the male connecting portion 206 while being electrically isolated therefrom via the male insulating member 210. The male insulating member 210 and the sealing ring 212 may be formed of silicone. The first section 50 may include one or more air inlets 215 through which air may be drawn and the pressure sensor may measure the air pressure resulting from the air drawn through the one or more air inlets 215.

The male connecting portion 206 of the first section 50 may, upon attachment of the first section 50 and the second section 100, electrically connect to cathode portion 106a of the second section 100. The first section 50 and the second section 100 may be attached by engaging the female connecting portion 106 of the second section 100 with the male connecting portion. 206 of the first section 50. The first section 50 may include a vaporizer 250. The vaporizer 250 may include a heating element (or heater) for vaporizing the pre-vapor formulation (see FIG. 3C).

From the above description of FIGS. 3A and 3B, it should be understood that the first section 50 and the second section 100 may be coupled together at a connection using a connector. The connector may include the male connecting portion 206 and the female connecting portion 106. According to example embodiments shown in FIGS. 3A and 3B, the male connecting portion 206 may be secured to the first section 50 while the female connecting portion 106 may be secured to the second section 100. The male connecting portion 206 may include a pair of mating arms extending from a rim of the male connecting portion. The pair of mating arms and the rim may define a pair of angled slots there between. A terminus of each of the pair of angled slots includes an enlarged socket end. The female connecting portion 106 is secured to the first section 50. For example, when the male connecting portion 206 is secured to the second section 100, the female connecting portion 106 is secured to the first section 50 (and vice versa). The female connecting portion 106 may include an inner surface and a pair of lugs on the inner surface. The female connecting portion 106 is configured to longitudinally and rotationally receive the pair of mating arms of the male connecting portion 206 so as to engage each of the pair of lugs of the female connecting portion 106 within the enlarged socket end of each of the pair of angled slots of the male connecting portion 206 to electrically couple the first section 50 and the second section 100.

FIG. 3C illustrates a close-up cross-sectional view of an example embodiment of the cartridge section shown in FIG. 3B within the dashed line. As shown in FIG. 3C, a heater 252 of the vaporizer 250 may be electrically connected to a body 220 of the male connecting portion 206 and the male anode 208 at connection points 255 and 260, respectively.

With reference to FIGS. 3B and 3C, the housing barrel 202 may include a reservoir 290 with porous materials 270 and 280. The reservoir 290 and the porous materials 270 and 280 may contain the pre-vapor formulation. A density of the porous material 270 may be greater than a density of the porous material 280. The housing barrel 202 may include a vaporizer 250. The vaporizer 250 may include a porous element 251 in fluid communication with the pre-vapor formulation contained within the reservoir 290. The vaporizer 250 may include a heating element (or heater) 252 for vaporizing the pre-vapor formulation contained in the porous element 251. A portion of the heater 252 may be coiled around the porous element 251 while two electrical leads of the heater 252 extend to connection points 255 and 260, respectively. The housing barrel 202 may include an inner tube 265 defining central air channel 275 to allow for air flow between air outlets 295 of the mouth piece 204 and the air inlets 215. The vaporizer 250 may be arranged in the air channel 275 such that vapor generated by the vaporizer may flow toward the mouthpiece 204.

Figure 3D:
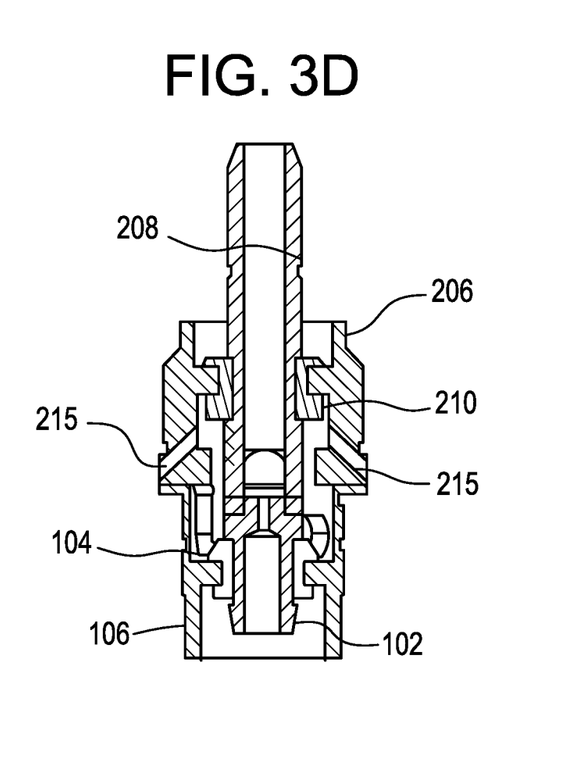
FIG. 3D illustrates a cross sectional view of a connection area between the cartridge section and the reusable section in FIG. 1.

FIG. 3D illustrates a cross sectional view of a connection area between the first section and the second section in FIG. 1. FIG. 3D shows the electrical connection between male anode 208 and female anode 102, and the electrical connection between the male connecting portion 206 and the cathode portion 106.

With reference to FIGS. 3A-3D, electrical connection between the anode 110b of the power supply 110 and the heater 252 in the first section 50 may be established through the PCB 116, the female anode 102 in the second section 100, male anode 208 in the first section 50, and a connection point 260 on the male anode 208 with a first electrical lead of the heater 252. Similarly, electrical connection between the cathode 110a of the power supply 110 and the heater 252 may be established through the PCB 116, the cathode portion 106a of the connecting portion 106, the male connecting portion 206, and a connection point 255 on the body 220 of the male connecting portion 206 with a second electrical lead of the heater 252. The connection points 255 and 260 may be achieved by, for example, spot welding or soldering the two electrical leads of the heater 252. The anode 110b is connected to the circuitry on the circuit board 116 by a battery wire 126. The circuit board 116 is connected to the cathode portion 106a by a wire 128.

Figure 4:
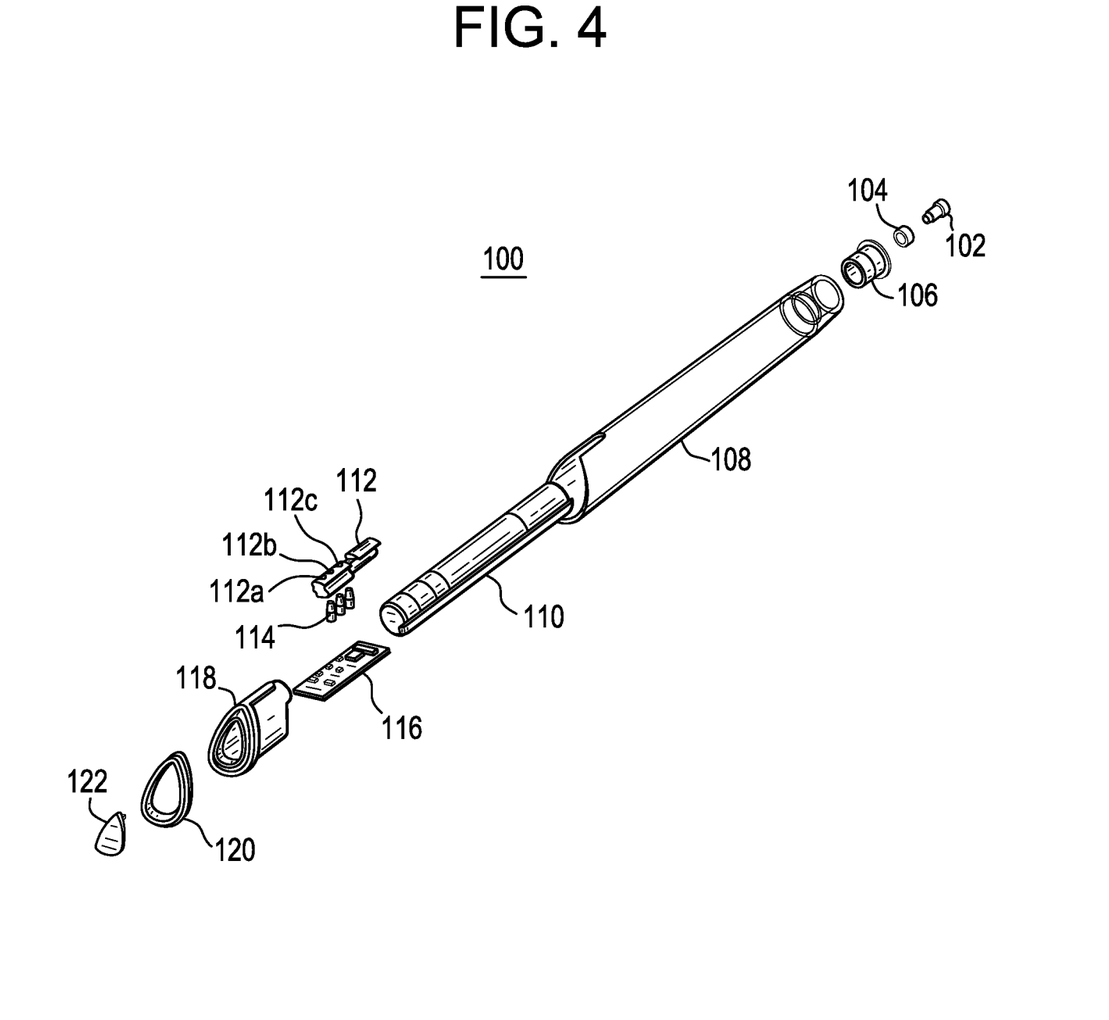
FIG. 4 illustrates an exploded view of an example embodiment of the reusable section shown in FIG. 1.

FIG. 4 illustrates an exploded view of the second section in FIG. 1. As shown in FIG. 4, the light pipe (or light article) 114 may be fitted to be inserted in cylindrical bores 112a, 112b and 112c of the light pipe assembly 112.

Figure 5:
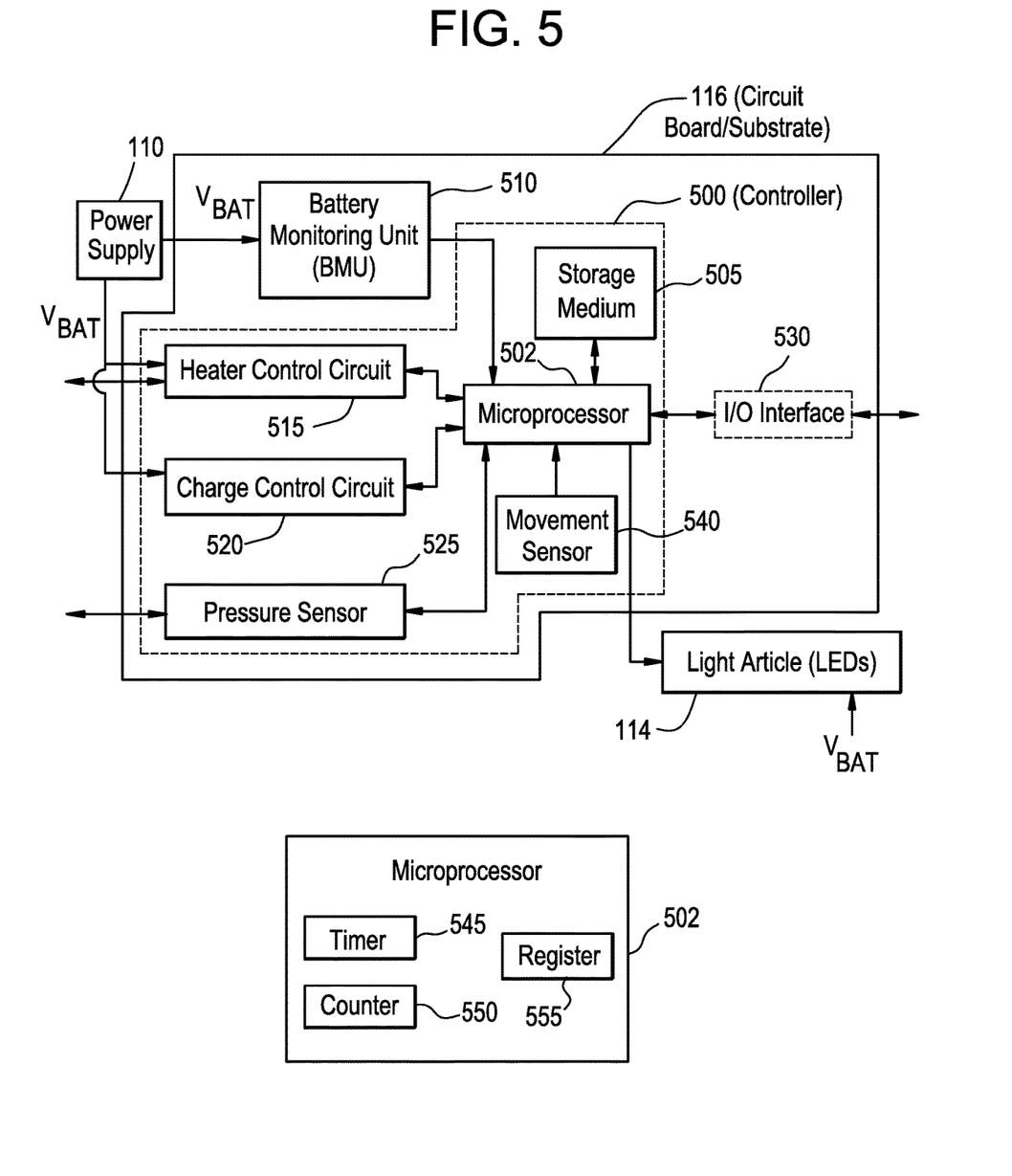
FIG. 5 illustrates an example embodiment of a circuit board of the electronic vaping device shown in FIG. 1.

FIG. 5 illustrates a block diagram of the PCB 116, according to an example embodiment.

As shown, the circuit board 116 may include a controller 500 and a battery monitoring unit (BMU) 510. In some example embodiments, the circuit board 116 includes an external device input/output interface 530. The I/O interface 530 may be a Bluetooth interface, for example.

The controller 500 includes a microprocessor 502, a computer-readable storage medium 505, a heater control circuit 515, a charge control circuit 520, a pressure sensor 525, and a movement sensor 540. Although not explicitly shown, it should be understood that the movement sensor 540 may be included as separate from the controller 500.

The controller 500 performs features of the second section 100, as well as the entire e-vaping device 10, such as controlling the heater, interfacing with an external charger and monitoring the pressure within the e-vaping device 10 to determine whether an adult vaper has applied a negative pressure. The controller 500 may be hardware, firmware, hardware executing software or any combination thereof. For example, the controller 500 may be one or more Central Processing Units (CPUs), digital signal processors (DSPs), one or more circuits, application-specific-integrated-circuits (ASICs), field programmable gate arrays (FPGAs), and/or computers or the like configured as special purpose machines to perform the functions of the controller 500.

For instance, if the controller 500 is a processor executing software, the controller 500 executes instructions stored in the computer readable storage medium 505 to configure the processor as a special purpose machine.

Furthermore, as shown in the example embodiment of FIG. 5, the controller 500 may be a combination of hardware and a processor executing software. As shown, hardware elements may include the computer-readable storage medium 505, the heater control circuit 515, the charge control circuit 520, the pressure sensor 525, and the movement sensor 540. As shown, the microprocessor 502 is configured to control the operation of the hardware elements described above by executing software stored on the storage medium 505.

The microprocessor (or control circuitry) 502 may be hardware, firmware, hardware executing software or any combination thereof. For example, the controller 500 may include one or more Central Processing Units (CPUs), digital signal processors (DSPs), one or more circuits, application-specific-integrated-circuits (ASICs), field programmable gate arrays (FPGAs), and/or computers or the like configured as special purpose machines to perform the functions of the microprocessor 502.

For instance, as shown in FIG. 5, if the microprocessor 502 is a processor executing software, the microprocessor 502 executes instructions stored in the computer readable storage medium 505 to configure the processor as a special purpose machine.

Furthermore, the microprocessor 502 may be a combination of hardware and a processor executing software. For example, as shown in FIG. 5, the microprocessor 502 includes a timer 545, a counter 550, and a register 555. Functions of these elements will be described in more detail below with reference to FIG. 6.

As disclosed herein, the term "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable storage medium" may include, but is not limited to, portable or fixed storage devices, optical storage devices, and various other mediums capable of storing, containing or carrying instruction(s) and/or data.

As shown in FIG. 5, the power supply 110 supplies a voltage $V_{BAT}$ to the heater control circuit 515, the charge control circuit 520 and the light article 114. Based on the voltage $V_{BAT}$ and data (or control signals) from the microprocessor 502, the light article 114 produces a light or series of lights indicating a status of the e-vaping device 10.

The heater control circuit 515 and the charge control circuit 520 are controlled by the microprocessor 502 and transmit receive data to and from the microprocessor 502.

More specifically, the heater control circuit 515 is configured to control a voltage supplied to the heater of the first section 50 based on a pulse-width modulation signal and an enable signal from the microprocessor 502. For example, when the microprocessor 502 detects that the first section 50 and 100 are connected, the heater control circuit 515 is configured to monitor a voltage across the heater and a current across the heater. The heater control circuit 515 is configured to feedback the monitored voltage and current across the heater to the microprocessor 502. The microprocessor 502 is then configured to adjust the pulse-width modulation signal based on the feedback from the heater control circuit 515.

The charge control circuit 520 acts as an interface between an external charger and the second section 100. More specifically, upon connecting to the charger, the charger sends a series of voltage pulses to the charge control circuit 520. The microprocessor 502 determines whether the series of voltage pulses is a correct series. If the series is determined by the microprocessor 502 to be correct, the microprocessor 502 instructs the charge control circuit 520 to generate a responding series of voltages such that if the charger sees the correct response, the charger begins charging the power supply 110.

The BMU 510 monitors a voltage $V_{BAT}$ generated by the power supply 110. If the voltage $V_{BAT}$ is within a set range (e.g., between 2.5V and 4.3V), the BMU 510 supplies the voltage $V_{BAT}$ to the microprocessor 502. If the voltage $V_{BAT}$ is not within the set range, the BMU 510 prevents power being supplied to the microprocessor 502.

The microprocessor 502 includes a voltage regulator to convert the voltage $V_{BAT}$ to another voltage $V_{DD}$. The microprocessor 502 supplies the voltage $V_{DD}$ to the pressure sensor 525.

The pressure sensor 525 may be a microelectromechanical system (MEMS) sensor that is a true pressure sensor. The microprocessor 502 uses the MEMS pressure sensor 525 to determine whether an adult vaper has applied a negative pressure on the e-vaping device 10. When the microprocessor 502 detects an adult vaper applying a negative pressure, the microprocessor 502 controls the heater control circuit 515 to begin a heating process for the heater to create a vapor by vaporizing the pre-vapor formulation.

By using a true MEMS pressure sensor 525, the microprocessor 502 may quickly determine a negative pressure from an adult vaper. Moreover, a MEMS pressure sensor may occupy less space than a differential pressure sensor because the MEMS pressure sensor 525 can be mounted directly on the circuit board 116.

The MEMS pressure sensor 525 may be an MS5637-02BA03 Low Voltage Barometric Pressure Sensor, for example.

Alternatively, the pressure sensor 525 may be a differential pressure sensor. Differential pressure sensors measure two air pressures, one ambient and one that changes. The differential pressure sensor is generally set on an end of the device and put into a gasket that seals one side of the sensor from another side of the sensor. When an adult vaper applies a negative pressure, the sealed side of the differential pressure sensor detects a pressure drop (vacuum), while the ambient side detects less of a drop due to the exposure by not being sealed. The differential pressure sensor then provides a differential signal.

In one example embodiment, the various elements of the controller 500 and the microprocessor 502 communicate using an Inter-Integrated Circuit (I²C) interface.

The movement sensor 540 may be a sensor capable of detecting movement (e.g., movement events) of the e-vaping device 10. For example, the movement sensor 540 may be a single-axis or multi-axis accelerometer that detects a magnitude and/or a direction of proper acceleration (or g-force). The accelerometer may operate according to piezoelectric, piezoresistive, and/or capacitive principles. The accelerometer may be a MEMS device. Detected movements may include movements of the e-vaping device 10 by an adult vaper such as taps on the e-vaping device 10, waving of the e-vaping device 10, swivels of the e-vaping device 10, etc. The movement sensor 540 may also detect an orientation of the e-vaping device 10. The controller 500 may operate power consuming elements of the e-vaping device 10 based on an output signal of the movement sensor 540. The power consuming elements may include at least one of a battery level indicator for indicating a level of the battery 110 (e.g., light article 114), a lock-out circuit for locking and unlocking the e-vaping device 10, and an indicator for indicating an amount of the pre-vapor formulation (e.g., light article 114), the vaporizer 250, etc.

The controller 500 may operate the e-vaping device 10 in a sleep mode, a standby mode, and an active mode. The active mode may be a mode in which the controller 500 activates the heater 252 (e.g., during a puff by an adult vaper). In the active mode, the microprocessor 502 sends read requests to the pressure sensor 525 at a first frequency to obtain pressure readings from the pressure sensor 525. The standby mode may be a mode in which the microprocessor 502 reduces a frequency of the read requests sent to the pressure sensor 525 compared to the active mode. Thus, the standby mode may reduce power consumption of the e-vaping device 10 compared to the active mode. The sleep mode may be a mode in which the microprocessor 502 reduces a frequency of the read requests sent to the pressure sensor 525 compared to the standby mode. Alternatively, in the sleep mode, the microprocessor 502 may turn off the pressure sensor 525 or terminate the read requests altogether, effectively disabling the pressure sensor 525. In any one of the sleep mode, the standby mode, and the active mode, a frequency of read requests sent by the microprocessor 502 may defined by an adult vaper and/or a design parameter set based on empirical evidence.

It should be understood that the controller 500 may be able to disable the pressure sensor 525 (e.g., using a switch) if the microprocessor 502 uses output of the movement sensor 540 to activate the vaporizer 250. For example, the microprocessor 502 may disable the pressure sensor 525 if the e-vaping device 10 is operating in a low power state of the active mode. Alternatively, the movement sensor 540 may replace the function of the pressure sensor 525 in that the microprocessor 502 may use output of the movement sensor 540 to determine when to activate the vaporizer 250.

Thus, according to at least one example embodiment, the controller 500 does not include the pressure sensor 525. In all of the above cases, power consumption may be reduced because the movement sensor 540 may consume less power than the pressure sensor 525.

Figure 6:
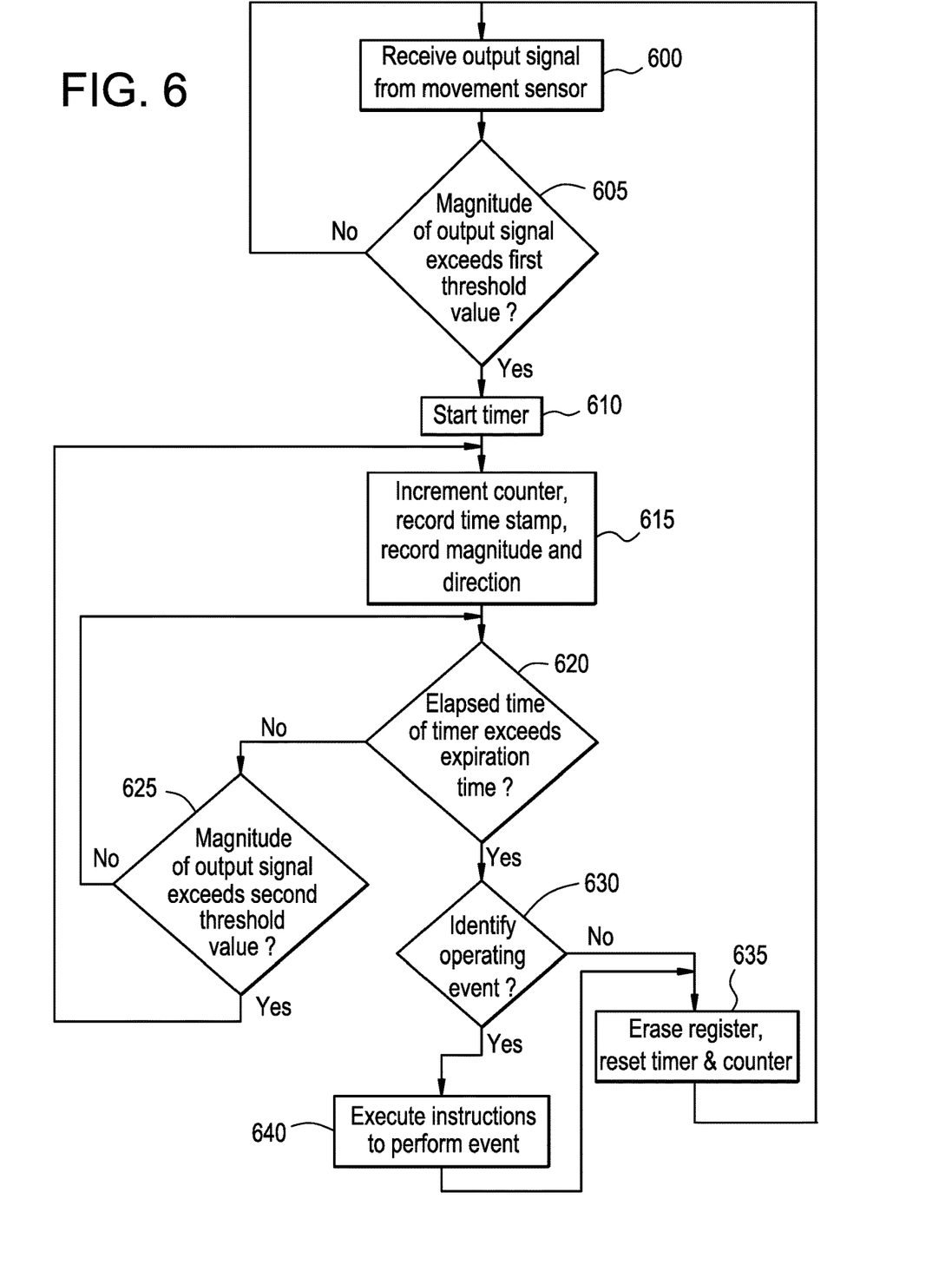
FIG. 6 a flow chart illustrating an example method of operating the controller shown in FIG. 5.

FIG. 6 a flow chart illustrating an example method of operating the controller shown in FIG. 5. For example, FIG. 6 shows operations of the controller 500 from the perspective of microprocessor 502.

In operation 600, the microprocessor 502 receives an output signal from the movement sensor 540. A magnitude (e.g., of a voltage) of the output signal may vary according to a movement of the e-vaping device 10. For example, if the e-vaping device 10 is at rest, a magnitude of the output signal may be less than a magnitude of the output signal if the e-vaping device 10 is tapped by an adult vaper (or experiencing other movement). However, example embodiments are not limited thereto.

If the movement sensor 540 is a multi-axis accelerometer, the output signal may include a component for each axis of the accelerometer (i.e., a component for each of x, y, and z axes). Thus, according to at least one example embodiment, the magnitude of the output signal may be measured by averaging the magnitudes of the components (e.g., two or three of the components). Alternatively, the microprocessor 502 may monitor each component of the output signal separately so that the operations of FIG. 6 are performed with respect to the magnitude of a single component. Thus, it should be understood that a "magnitude of the output signal" applies to any of the above possibilities, depending on implementation.

In operation 605, the microprocessor 502 determines whether a magnitude of the output signal exceeds a first threshold value. That is, the microprocessor 502 may detect movement events based on a magnitude of the output signal. Example embodiments are not limited to determining whether a magnitude of the output signal exceeds a threshold. According to at least one example embodiment, the microprocessor may 502 determine whether a change in magnitude of the output signal exceeds a threshold. Further, the microprocessor 502 may also be able to detect a direction of movement based on the change in magnitude of the output signal.

The first threshold value may be defined by an adult Taper and/or be a design parameter set based on empirical evidence. For example, if the output signal is a voltage signal, the microprocessor 502 may determine whether the voltage signal exceeds a first threshold voltage level. If not, the microprocessor 502 continues to receive the output signal from the movement sensor 540 in operation 600. If the microprocessor 502 determines that the magnitude of the output signal exceeds the first threshold value, then the microprocessor 502 starts a timer 545 in operation 610.

In operation 615, the microprocessor 502 increments a counter 550 to indicate an instance of the output signal exceeding the first threshold value in operation 605. In operation 615, the microprocessor 502 may also track when the counter 550 is incremented by recording, for example, time stamps. Further still, the microprocessor 502 may record the magnitude and direction of the detected movement event. The time stamps, the magnitude and the direction may be stored in the register 555 as this information may be useful for identifying an operating event (see discussion of operation 630).

In operation 620, the microprocessor 502 determines whether an elapsed time of the timer 545 exceeds an expiration time. The expiration time may be defined by an adult vaper and/or a design parameter set based on empirical evidence. For example, the expiration time may be selected according to how long it is desired for the microprocessor 502 to monitor the output signal upon detecting a first instance of the magnitude of the output signal exceeding the first threshold value in operation 605. If the microprocessor 502 determines that the elapsed time of the timer 545 does not exceed the expiration time, then the microprocessor 502 determines whether the output signal exceeds a second threshold value in operation 625. If so, then the microprocessor 502 returns to operation 615 to increment the counter 550. The second threshold value may be the same as the first threshold value. However, the second threshold value may be less than or greater than the first threshold value if desired. The second threshold may be defined by an adult vesper and/or a design parameter set based on empirical evidence. For example, the first and second thresholds may be adjusted by an adult vesper through the interface 530.

If the microprocessor 502 determines that the second threshold value is not exceeded in operation 625, the microprocessor 502 does not increment the counter 550 and returns to operation 620 to determine whether the elapsed time of the timer 545 has exceeded the expiration time.

It should be understood that operations 600-625 result in the microprocessor 502 being able to count (via the counter 550) a number of times that the output signal exceeds one or more threshold values within the expiration time period. That is, the microprocessor 502 may detect a number of movement events (e.g., taps, swivels, etc.) of the e-vaping device 10 within a particular time period.

If the microprocessor 502 determines that the elapsed time of the timer 545 exceeds the expiration time period in operation 620, the microprocessor 502 attempts to identify an operating event in operation 630 based on content of the counter 550. In view of operations 600-625, the content of the counter 550 should indicate a number of movement events that were detected before the elapsed time of the timer 545 exceeded the expiration time. Thus, the microprocessor 502 identifies an operating event based on the counted number of detected movement events. Alternatively, the microprocessor 502 is configured to identify the operating event based on the counted number of movement events and at least one of the first and second threshold values, the expiration time, the magnitude of the output signal, a direction of the movement, and time stamps associated with the counted number of detected movement events.

The operating event may be a function of the e-vaping device 10, for example, a battery level indication function that indicates a level of the battery 110, a lock-out circuit function for locking and unlocking the e-vaping device 10, a pre-vapor formulation level indicator function that indicates a level of the pre-vapor formulation in the cartridge 50, a function that activates the vaporizer 250, or any other functionality capable of being performed by the e-vaping device 10 (e.g., power on and warm up, increase heater voltage, etc.). The microprocessor 502 may consult a table (e.g., a lookup table (LUT)) stored in the storage medium 505 to identify the operating event. For example, the microprocessor 502 may attempt to identify an operating event by correlating the number of movement events indicated by the counter 550 with a table stored in the storage medium 505.

The table may include entries that associate a counted number of movement events with a particular operating event of the e-vaping device 10. For example, the table may include entries to indicate that two counted movement events should indicate to initiate an operating event that checks a battery level of the e-vaping device 10, three counted movement events should indicate to initiate an operating event that activates the vaporizer 250, and so on. The table entries may be defined by an adult vaper and/or a design parameter set based on empirical evidence. The table entries may also be adjusted by an adult vaper through the interface 530. If the movement sensor 540 is a multi-axis accelerometer and if the microprocessor 502 is monitoring multiple components of the output signal, the table may include a number of entries associated with each axis. For example, a number of movement events detected using an x-axis component of the output signal may correspond to a different operating event than a same number of movement events detected using a y-axis component of the output signal. Thus, the microprocessor 502 may execute the operations of FIG. 6 in three parallel manners, one for each axis of the accelerometer.

The microprocessor 502 may identify the operating event based on the counted number of detected movement events and at least one of the expiration time, the at least one threshold value, the magnitude of the output signal, a direction of the movement, and time stamps associated with the counted number of detected movement events (i.e., time stamps stored in the register 555 that indicate when the counter 550 is incremented). For example, the first and second thresholds may be associated with a particular expiration time so that adjusting the thresholds also adjusts the expiration time or vice versa. The time stamps may allow for the microprocessor 502 to determine the interval between each detected movement event. The microprocessor 502 may use some or all of this information in addition to the counted number of movement events to identify the operating event. This may allow for the microprocessor 502 to identify different operating events for a same number of counted movement events. For example, the microprocessor 502 may identify two quick taps (or movement events) on the e-vaping device 10 as a different operating event than two taps (or movement events) separated by a relatively long interval. Accordingly, the table may include columns titled "Counted Number of Movement Events," "Operating Event," "Threshold Value(s)," "Expiration Time," "Magnitude of Output Signal," "Direction of Movement," and "Interval between Detected Movement Events" with corresponding information about each category being listed in the columns. The information in the table may be retrievable and/or adjustable by an adult vapor via interface 530 and/or a design parameter set based on empirical evidence.

If, in operation 630, the microprocessor 502 does not identify the operating event (e.g., because the counted number of movement events does not have a corresponding entry in the table), then the microprocessor 502 resets the timer 545 and the counter 550 in operation 635 before returning to operation 600. If, in operation 630, the microprocessor 502 identifies an operating event, then the microprocessor 502 executes instructions to perform the identified operating event. For example, if the microprocessor 502 determines that the counted number of movement events matches an entry in the table associated with an operating event that activates the vaporizer 250, then the microprocessor 502 executes instructions to cause the heater control circuit 515 to supply power to the vaporizer 250. According to at least one example embodiment, the microprocessor 502 may disable the pressure sensor 525 (e.g., by opening a switch between the microprocessor 502 and the pressure sensor 525) upon activating the heater control circuit 515 to save power normally consumed by the pressure sensor 525. Thus, the microprocessor 502 supplies power to desired ones of the e-vaping device's power consuming elements based on the identified operating event. Power consuming elements may include any elements of the e-vaping device 10 that consume power such as a battery level indicator for indicating a level of the battery (e.g., the light article 114), a lock-out circuit for locking and unlocking the e-vapor device 10, and an indicator for indicating an amount of the pre-vapor formulation (e.g., the light article 114), etc.

After operation 640, the microprocessor 502 erases the register 555 and resets the timer 545 and the counter 550 in operation 635 before returning to operation 600.

It should be understood that causing the microprocessor 502 to execute instructions to perform the identified operating event in operation 640 may be conditioned upon other circumstances, such as an operating state of the e-vaping device 10. For example, if the battery of the e-vaping device 10 is below a threshold level, then the microprocessor 502 may cancel or postpone the identified operating event.

In view of the above, it should be understood that a controller and an e-vaping device according to at least one example embodiment may reduce the number of buttons on the e-vaping device, operate with reduced power consumption (e.g., in cases where an e-vaping device relies on output of the movement sensor instead of the puff sensor to activate the vaporizer), and/or provide convenient and customizable operating options.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. A controller for an e-vaping device, the controller comprising:
   a pressure sensor configured to detect application of negative pressure to the e-vaping device;
   a movement sensor configured to detect movement of the e-vaping device and output an output signal based on the movement;
   a memory configured to store instructions; and
   at least one processor configured to execute the instructions, the instructions including instructions for,
      controlling power supplied to power consuming elements of the e-vaping device in response to the pressure sensor detecting the application of negative pressure, the power consuming elements including a vaporizer, and
      when the e-vaping device is in a low power state, disabling the pressure sensor and replacing control of power supplied to the power consuming elements of the e-vaping device with the movement sensor, and controlling power supplied to the power consuming elements of the e-vaping device with the movement sensor by,
         in response to a magnitude of the output signal exceeding a first threshold value, counting a number of times that the magnitude of the output signal exceeds a second threshold value within a time interval associated with the second threshold value,
         detecting expiration of the time interval associated with the second threshold value,
         identifying, in response to detecting the expiration of the time interval, an operating event of a set of operating events based on the number of times that the magnitude of the output signal has exceeded the second threshold value within the time interval associated with the second threshold value, and
         controlling power supplied to the power consuming elements of the e-vaping device based on the operating event.

2. The controller of claim 1, wherein the movement sensor is an accelerometer.

3. The controller of claim 1, wherein the instructions include instructions for detecting a movement event resulting from the movement of the e-vaping device based on the magnitude of the output signal.

4. The controller of claim 1, wherein the instructions include instructions for consulting a table stored in a storage medium to identify the operating event.

5. The controller of claim 1, wherein the instructions include instructions for supplying power to at least one of the power consuming elements based on the operating event.

6. The controller of claim 5, wherein
   the at least one of the power consuming elements includes a battery level indicator, a lock-out circuit, an indicator, a sub-combination thereof or a combination thereof;
   the battery level indicator is configured to indicate a level of a battery;
   the lock-out circuit is configured to lock or unlock the e-vaping device; and
   the indicator is configured to indicate an amount of pre-vapor formulation in the e-vaping device.

7. An e-vaping device, comprising:
   a reservoir configured to store pre-vapor formulation;
   a vaporizer configured to heat pre-vapor formulation drawn from the reservoir;
   a power supply configured to supply power to power consuming elements of the e-vaping device, the power consuming elements including the vaporizer;
   a pressure sensor configured to detect application of negative pressure to the e-vaping device;
   a movement sensor configured to detect movement of the e-vaping device and output an output signal based on the movement;
   a memory configured to store instructions; and
   at least one processor configured to execute the instructions, the instructions including instructions for,
      controlling power supplied to the power consuming elements of the e-vaping device in response to the pressure sensor detecting the application of negative pressure, and
      when the e-vaping device is in a low power state, disabling the pressure sensor and replacing control of power supplied to the power consuming elements of the e-vaping device with the movement sensor, and controlling power supplied to the power consuming elements of the e-vaping device with the movement sensor by,
         in response to a magnitude of the output signal exceeding a first threshold value, counting a number of times that the magnitude of the output signal exceeds a second threshold value within a time interval associated with the second threshold value,
         detecting expiration of the time interval associated with the second threshold value,
         identifying, in response to detecting the expiration of the time interval, an operating event based on the number of times that the magnitude of the output signal has exceeded the second threshold value within the time interval associated with the second threshold value, and controlling the power supplied to the power consuming elements based on the operating event.

8. The e-vaping device of claim 7, wherein the movement sensor is an accelerometer.

9. The e-vaping device of claim 7, wherein the vaporizer includes,
a porous element in fluid communication with the reservoir, and
a heater configured to heat pre-vapor formulation in the porous element.

10. The e-vaping device of claim 7, wherein the instructions include instructions for detecting a movement event from the movement of the e-vaping device based on the magnitude of the output signal.

11. The e-vaping device of claim 7, wherein the instructions include instructions for consulting a table stored in a storage medium to identify the operating event.

12. The e-vaping device of claim 7, wherein the instructions include instructions for controlling the power supply to supply power to at least one of the power consuming elements based on the operating event.

13. The e-vaping device of claim 12, wherein
the at least one of the power consuming elements includes a battery level indicator, a lock-out circuit, an indicator, a sub-combination thereof or a combination thereof;
the battery level indicator is configured to indicate a level of a battery;
the lock-out circuit is configured to lock or unlock the e-vaping device; and
the indicator is configured to indicate an amount of pre-vapor formulation in the reservoir.

14. A method of operating an e-vaping device, the method comprising:
controlling power supplied to power consuming elements of the e-vaping device in response to a pressure sensor detecting application of negative pressure to the e-vaping device, the power consuming elements including a vaporizer;
when the e-vaping device is in a low power state, disabling the pressure sensor and replacing control of power supplied to the power consuming elements of the e-vaping device with a movement sensor, and controlling power supplied to the power consuming elements of the e-vaping device with the movement sensor by,
counting, in response to a magnitude of an output signal exceeding a first threshold value, a number of times that the magnitude of the output signal exceeds a second threshold value within a time interval associated with the second threshold value, the output signal is output based on detected movement of the e-vaping device;
detecting expiration of the time interval associated with the second threshold value;
identifying, in response to detecting the expiration of the time interval, an operating event based on the number of times that the magnitude of the output signal has exceeded the second threshold value within the time interval associated with the second threshold value; and
controlling power supplied to the power consuming elements of the e-vaping device based on the operating event.

15. The controller of claim 1, wherein
the movement sensor is a multi-axis accelerometer,
the output signal includes an x-axis component of the multi-axis accelerometer, a y-axis component of the multi-axis accelerometer, and a z-axis component of the multi-axis accelerometer, and
the magnitude of the output signal is a magnitude of the x-axis component, a magnitude of the y-axis component, a magnitude of the z-axis component, or any combination thereof.

16. The controller of claim 1, wherein the number of times that the magnitude of the output signal has exceeded the second threshold value is greater than 1.

17. The controller of claim 1, wherein when the e-vaping device is in a low power state, the movement sensor is configured to activate the vaporizer.

* * * * *